United States Patent
Berry et al.

(10) Patent No.: US 10,413,642 B2
(45) Date of Patent: Sep. 17, 2019

(54) SYSTEM FOR DYNAMIC CONTROL OF MEDICAL VACUUM

(71) Applicants: James Michael Berry, Nashville, TN (US); Steve Morris, Canton, MS (US)

(72) Inventors: James Michael Berry, Nashville, TN (US); Steve Morris, Canton, MS (US)

( * ) Notice: Subject to any disclaimer, the term of this patent is extended or adjusted under 35 U.S.C. 154(b) by 574 days.

(21) Appl. No.: 15/132,380

(22) Filed: Apr. 19, 2016

(65) Prior Publication Data

US 2016/0317725 A1 Nov. 3, 2016

Related U.S. Application Data

(60) Provisional application No. 62/179,125, filed on Apr. 28, 2015.

(51) Int. Cl.
*A61M 1/00* (2006.01)

(52) U.S. Cl.
CPC ......... *A61M 1/0035* (2014.02); *A61M 1/0025* (2014.02); *A61M 2205/13* (2013.01)

(58) Field of Classification Search
CPC .............. A61M 1/0035; A61M 1/0033; A61M 1/0031; A61M 1/0025; A61M 2205/13; A61C 17/043
See application file for complete search history.

(56) References Cited

U.S. PATENT DOCUMENTS

| 575,714 | A | 1/1897 | Heinzerling |
| 1,040,886 | A | 10/1912 | Claude |
| 1,508,043 | A | 9/1924 | Barrows |
| 3,348,538 | A | 10/1967 | Benzel |
| 3,517,521 | A | 6/1970 | Emerson |
| 3,592,191 | A | 7/1971 | Jackson |
| 3,714,942 | A | 2/1973 | Fischel et al. |
| 3,721,239 | A | 3/1973 | Myers |
| 3,800,793 | A | 4/1974 | Marrese et al. |

(Continued)

FOREIGN PATENT DOCUMENTS

| WO | 1998008583 | 3/1998 |
| WO | 2001024858 | 4/2001 |

OTHER PUBLICATIONS

"Gleanings for ATM'S", R.F. Cox and R.W. Sinnott, Nov. 1976, Sky and Telescope, pp. 376-381.

(Continued)

*Primary Examiner* — Adam Marcetich
*Assistant Examiner* — Jessica R Arble
(74) *Attorney, Agent, or Firm* — Bracewell LLP; Douglas W. Rommelmann

(57) ABSTRACT

A method and system of controlling medical suction is disclosed. The system comprises a vacuum regulator comprising a valve, wherein the first end of the regulator may be fluidly connected to a vacuum source and the second end of the regulator may be fluidly connected to a patient interface. The valve may comprise a small orifice or pathway, allowing fluid to pass from the second end of the regulator to the first end of the regulator while the valve is closed. The system may also comprise a flow detector, wherein the flow detector is capable of sensing when the patient interface is in contact with a liquid and cause the valve to open, thereby allowing full flow of fluids from the second regulator end to the first regulator end.

18 Claims, 2 Drawing Sheets

(56) References Cited

U.S. PATENT DOCUMENTS

| | | |
|---|---|---|
| 3,867,936 A | 2/1975 | Kelley |
| 3,941,573 A | 3/1976 | Chapel |
| 4,004,585 A | 1/1977 | Boehringer |
| 4,119,984 A | 10/1978 | Zajac |
| 4,127,163 A | 11/1978 | Reti |
| 4,172,662 A | 10/1979 | Vogel |
| 4,180,066 A | 12/1979 | Milliken et al. |
| 4,181,508 A | 1/1980 | Schmid et al. |
| 4,205,095 A | 5/1980 | Pike et al. |
| 4,219,020 A | 8/1980 | Czajkia |
| 4,246,015 A | 1/1981 | Styring |
| 4,251,127 A | 2/1981 | Yamaguchi |
| 4,259,303 A | 3/1981 | Nakaji et al. |
| 4,261,178 A | 4/1981 | Cain |
| 4,265,239 A | 5/1981 | Fischer et al. |
| 4,281,518 A | 8/1981 | Muller et al. |
| 4,291,689 A | 9/1981 | Hay |
| 4,312,339 A | 1/1982 | Thompson |
| 4,378,984 A | 4/1983 | Cheng et al. |
| 4,447,462 A | 5/1984 | Tafuri et al. |
| 4,451,273 A | 5/1984 | Cheng et al. |
| 4,527,558 A | 7/1985 | Hoenig |
| 4,538,605 A | 9/1985 | Gedeon et al. |
| 4,609,388 A | 9/1986 | Adler et al. |
| 4,633,890 A | 1/1987 | Carden |
| 4,653,493 A | 3/1987 | Hoppough |
| 4,676,239 A | 6/1987 | Humphrey et al. |
| 4,755,201 A | 7/1988 | Eschwey et al. |
| 4,768,347 A | 9/1988 | Manz et al. |
| 4,832,042 A | 5/1989 | Poppendiek et al. |
| 4,895,172 A | 1/1990 | Lindkvist |
| 4,905,685 A | 3/1990 | Olsson et al. |
| 4,928,685 A | 5/1990 | Gray |
| 4,936,667 A | 6/1990 | Rohr et al. |
| 4,945,906 A | 8/1990 | Lindkvist |
| 4,949,714 A | 8/1990 | Orr |
| 4,955,702 A | 9/1990 | Nakamura |
| 5,033,464 A | 7/1991 | Dicastilho |
| 5,044,361 A | 9/1991 | Werner et al. |
| 5,044,363 A | 9/1991 | Burkhart |
| 5,046,491 A | 9/1991 | Derrick |
| 5,046,492 A | 9/1991 | Stackhouse et al. |
| 5,062,270 A | 11/1991 | Haut et al. |
| 5,152,812 A | 10/1992 | Kovach |
| 5,161,061 A | 11/1992 | Ihara et al. |
| 5,205,843 A | 4/1993 | Kaschemekat et al. |
| 5,253,641 A | 10/1993 | Choate |
| 5,299,067 A | 3/1994 | Kutz et al. |
| 5,311,862 A | 5/1994 | Blasdell et al. |
| 5,323,623 A | 6/1994 | Carns et al. |
| 5,339,642 A | 8/1994 | Laukhuf |
| 5,345,928 A | 9/1994 | Lindkvist |
| 5,370,110 A | 12/1994 | Corn |
| 5,398,675 A | 3/1995 | Henkin et al. |
| 5,419,317 A | 5/1995 | Blasdell |
| 5,419,768 A * | 5/1995 | Kayser ................ A61M 1/0031 128/205.19 |
| 5,450,728 A | 9/1995 | Vora et al. |
| 5,482,033 A | 1/1996 | Engle |
| 5,485,307 A | 1/1996 | Kim |
| 5,491,589 A | 2/1996 | Haymond |
| 5,507,282 A | 4/1996 | Younes |
| 5,520,119 A | 5/1996 | Eisenberg |
| 5,520,169 A | 5/1996 | Georgieff et al. |
| 5,561,555 A | 10/1996 | Meier et al. |
| 5,568,910 A | 10/1996 | Koehler et al. |
| 5,676,133 A | 10/1997 | Hickle et al. |
| 5,678,540 A | 10/1997 | Kock et al. |
| 5,694,924 A | 12/1997 | Cewers |
| 5,715,813 A | 2/1998 | Guevrekian |
| 5,740,682 A | 4/1998 | Lavie |
| 5,759,504 A | 6/1998 | Kanno et al. |
| 5,769,072 A | 6/1998 | Olsson et al. |
| 5,819,555 A | 10/1998 | Engdahl |
| 5,835,289 A | 11/1998 | Berry |
| 5,928,411 A | 7/1999 | Falb et al. |
| RE36,460 E | 12/1999 | Klatz et al. |
| 6,030,591 A | 2/2000 | Tom et al. |
| 6,072,524 A | 6/2000 | Davis et al. |
| 6,076,524 A | 6/2000 | Corn |
| 6,080,226 A | 6/2000 | Dolan et al. |
| 6,082,133 A | 7/2000 | Barclay et al. |
| 6,131,571 A | 10/2000 | Lampotang et al. |
| 6,134,914 A | 10/2000 | Eschwey et al. |
| 6,158,434 A | 12/2000 | Lugtigheld et al. |
| 6,206,002 B1 | 3/2001 | Lambert |
| 6,237,596 B1 | 5/2001 | Bohmfalk |
| 6,328,036 B1 | 12/2001 | Emtell et al. |
| 6,357,437 B1 | 3/2002 | Jacques |
| 6,374,635 B1 | 4/2002 | Hayakawa et al. |
| 6,405,539 B1 | 6/2002 | Stach et al. |
| 6,475,266 B2 | 11/2002 | Hayashi et al. |
| 6,488,028 B1 | 12/2002 | Lambert |
| 6,490,883 B2 | 12/2002 | Trembley et al. |
| 6,513,345 B1 | 2/2003 | Betting et al. |
| 6,536,430 B1 | 3/2003 | Smith |
| 6,729,329 B2 | 5/2004 | Berry |
| 6,736,140 B1 | 5/2004 | Baczkowski |
| 6,776,158 B1 | 8/2004 | Anderson et al. |
| 6,863,067 B2 | 3/2005 | Loncar |
| 7,204,821 B1 * | 4/2007 | Clare ................ A61M 1/0031 137/102 |
| 7,596,965 B2 | 10/2009 | Berry et al. |
| 7,628,034 B2 | 12/2009 | Berry et al. |
| 7,644,594 B2 | 1/2010 | Berry et al. |
| 7,669,438 B2 | 3/2010 | Berry et al. |
| 2003/0185735 A1 | 10/2003 | Hotta et al. |
| 2004/0122365 A1 * | 6/2004 | Stinson ............... A61M 1/0031 604/119 |
| 2005/0155380 A1 | 7/2005 | Rock |
| 2009/0043268 A1 * | 2/2009 | Eddy ................... A61M 1/0037 604/290 |
| 2011/0071483 A1 * | 3/2011 | Gordon ............... A61M 1/0031 604/319 |
| 2014/0299544 A1 * | 10/2014 | Wilt ................... A61M 1/1601 210/646 |

OTHER PUBLICATIONS

Brown AC, Canosa-Mas CE, Parr AD, et al.: Tropospheric lifetimes of halogenated anaesthetics. Nature 1989; 341: 635-637.

Langbein T, Sonntag H, Trapp D, et al.: Volatile anaesthetics and the atmosphere: atmospheric lifetimes and atmospheric effects of halothane, enflurane, isoflurane, desflurane and sevoflurane. Br J Anaesth 1999; 82: 66-73.

McCulloch, A.: Letter to Editor regarding Langbein, et al. 1999 paper. Br J Anaesth 2000; 84 (4): 534-36.

Dunn, R.F; Zhu, M., Srinivas B.K. and El-Halwagi, M.M. (1995), Optimal Design of Energy-Induced Separation Networks for VOC Recovery, AIChE Symp. Ser., 90(303), 74-85, NY: AIChE.

* cited by examiner

SYSTEM FOR DYNAMIC CONTROL OF MEDICAL VACUUM

CROSS-REFERENCE TO RELATED APPLICATIONS

This application claims the benefit of U.S. Provisional Application Ser. No. 62/179,125 filed Apr. 28, 2015. Applicant incorporates by reference herein Application Ser. No. 62/179,125 in its entirety.

BACKGROUND OF THE INVENTION

1. Field of the Invention

Embodiments described herein are employed for various patient-care functions. More particularly, embodiments relate to apparatus and methods for enhancing control over medical vacuum systems.

2. Description of the Related Art

Healthcare facilities provide medical vacuum or suction for various essential patient-care functions, such as removal of bodily fluids, aspirating secretions from airways, emptying stomach contents, and many other similar uses. Many of these needs are intermittent but unpredictable. Medical facilities may install centrally-located vacuum producers (e.g., pumps) and receivers with networks of piping to distribute this vacuum similar to the way medical gases are centrally located and distributed.

At the end-user level, outlets are provided at patient-care locations to which are attached regulators and flow controls to regulate the amount of suction according to need. Frequently, these controls are left on through neglect or the perception that they should be instantly available should an urgent need arise. This practice is wasteful of energy and produces excessive wear on the central pump(s).

SUMMARY OF THE INVENTION

Described is a system for sensing when a medical vacuum is required by the end-user at a patient-care location by detecting a small change in pressure in a vacuum device. This pressure change opens a solenoid or valve, allowing full vacuum flow to occur. In some embodiments, after a preset time, the solenoid closes, thus conserving the capacity of the facility's vacuum producing device.

An electrically-actuated solenoid or valve may be utilized to stop the flow of vacuum at multiple locations in order to manage the vacuum capacity at the facility as a whole. Reuse of the vacuum at a patient-care location may be required in some time-sensitive situations. For this reason, ease in restarting the full vacuum flow may be critical.

If a small pathway or orifice is machined into the valve body of a valve or electrical solenoid, even when the solenoid is in the closed position a small amount of air will flow through the pathway. Alternatively, a separate side-channel that bypasses the valve may be used to allow a small amount of air to flow even while the valve is closed. With the valve or solenoid closed, pressure in the patient side of the suction apparatus approaches ambient. If a sensitive transducer is placed on the patient side of this "leaky" valve, attempted use of the vacuum will be detected as a small change in ambient patient-side pressure by the transducer. This change in pressure may be used to generate an electrical signal. This electrical signal may be used to trigger a timing circuit to open the solenoid and allow full vacuum flow for a pre-determined period of time.

DESCRIPTION OF THE PREFERRED EMBODIMENTS

Figure 1:
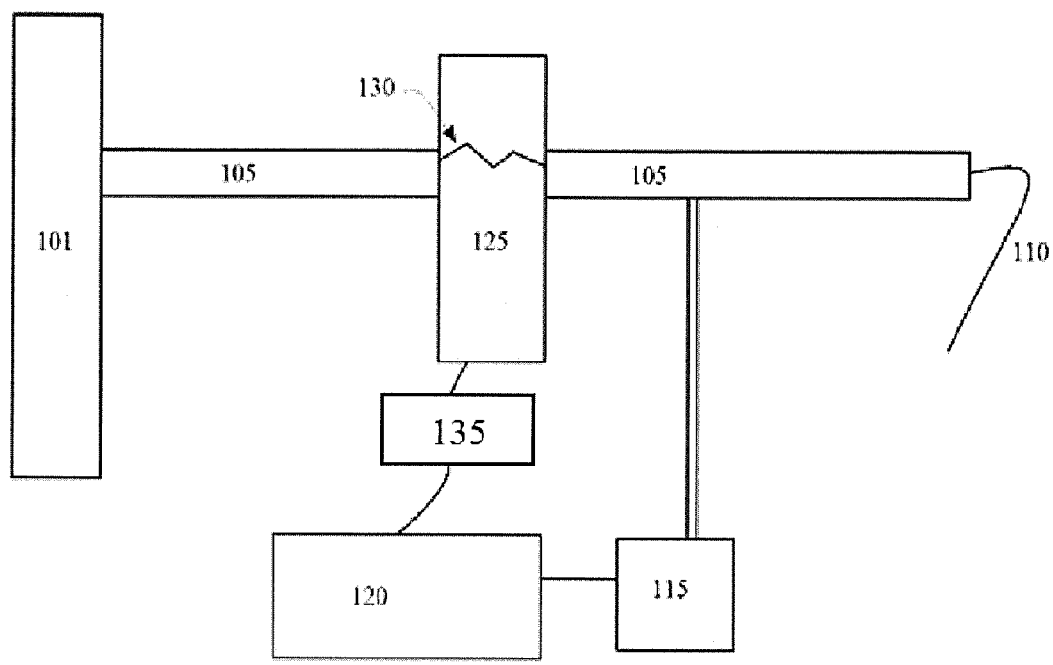
FIG. 1 is a block diagram of one embodiment of the disclosed system.

The embodiment disclosed in FIG. 1 may comprise: an electrically-actuated vacuum-control solenoid or valve 125 with a small bypass pathway 130 or orifice that produces a leak even when the solenoid 125 is closed; a sensitive pressure transducer 115; a timing circuit 120 triggered by the transducer; and a control circuit 135 to control power to the solenoid. This system might be integrated into wall-mounted vacuum inlets, or it might be a separate device attached to a fixed or portable vacuum source 101.

At each patient-care location, a modified vacuum regulator 105 may be installed incorporating a valve 125 fluidly-connected to a vacuum source 101 at the first end of the regulator 105 and a patient interface 110 at the second end of the regulator. The patient interface 110 will frequently include a fluid trap for capturing bodily fluids before any air is suctioned into the regulator 105. The fluid trap allows for easy disposal of trapped bodily fluids and prevents contamination of the regulator 105. If the valve 125 or the regulator 105 is modified by the creation of a small pathway 130 or orifice, a continuous small flow of air will occur from the second end of the regulator 105 to the first end even when the valve 125 is closed. The pathway 130 or orifice may preferentially be in the size range of 0.01-0.04 inches or may be as large as 0.1 inches or as small as 0.001 inches depending on the application.

A sensitive flow detector 115 connected between the valve 125 and the second end of the regulator 105 will sense the insertion of the patient interface 110 into a liquid as a brief change in flow through the orifice 130 or a slight change in pressure between the second regulator end and the valve 125. The flow detector 115 may generate an electrical signal in response to detecting this slight change in pressure. This may then actuate the valve 125 to open and allow full flow of air and liquid from the second end of the regulator 105 to the first end. After a predetermined time, preferentially 10-30 seconds, but as long as 1 minute and as short as 5 seconds, the valve 125 may close and full flow will cease. The predetermined time may be as long as 3 minutes or as long as 10 minutes or may be as short as 3 seconds or as short as 0.5 seconds.

In some embodiments, flow detector 115 may be connected to the patient interface 110 directly. The flow detector 115 may also be connected between the patient interface 110 and the second end of the regulator 105.

This system has the feature of allowing medical suction to be almost instantly available when the patient interface 110 is placed in a liquid (e.g., a bodily fluid) while conserving the full vacuum capability of the vacuum system for other users when not immediately needed.

This system might be integrated into a permanently wall-mounted vacuum source point or be embodied into a movable suction regulator mounted temporarily on a floor stand, anesthesia machine, endoscopy unit or other medical device.

The valve might be electrically or mechanically actuated while the flow detector could be mechanical, hydraulic, electric, magnetic, or based on differential pressures.

The preferred embodiment might consist of: an electrically-actuated solenoid valve 125 with a small orifice 130 producing a continuous leak, fluidly-coupled to a sensitive differential pressure transducer 115 (sensing instantaneous changes in flow), and a timing circuit 120 with an associated electrical power supply.

In some embodiments, the default position of the solenoid valve 125 will be open, thereby producing a fail-safe effect. If the power to the control circuit 135, timing circuit 120, flow detector 115 or any other powered aspect of the device should fail, the valve 125 will default to the open position allowing full suction.

Figure 2:
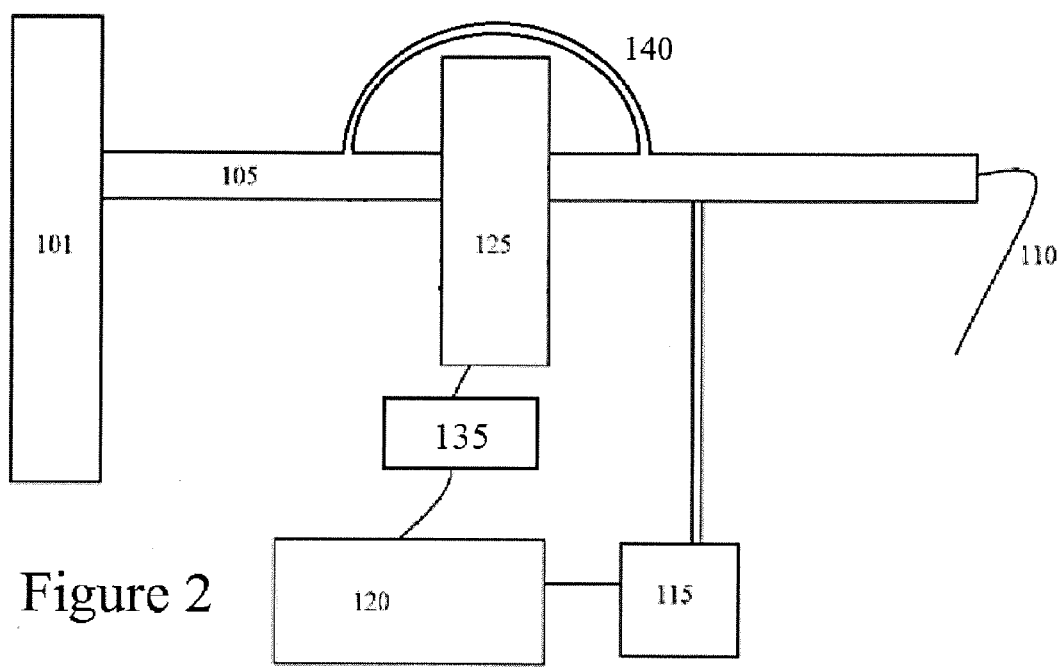
FIG. 2 is a block diagram of an alternative embodiment of the disclosed system.

In an alternative embodiment shown in FIG. 2, the pathway which allows a small transfer of air while the valve 125 is closed may be an independent pathway 140 connecting the second end of the regulator 105 to the first side of the regulator 105. In this embodiment, the valve 125 which generally blocks access to the suction may be unaltered and fully prevent communication between the first end of the regulator 105 and the second end of the regulator 105 except through alternative pathway 140. The independent pathway 140 allows the flow detector 115 to operate as described above even with the unaltered valve 125 fully closed.

Disclosed embodiments relate to a medical suction regulator apparatus comprising a vacuum regulator 105. The vacuum regulator 105 may comprise a valve 125, wherein the first end of the regulator 105 may be fluidly connected to a vacuum source 101 and the second end of the regulator 105 may be fluidly connected to a patient interface 110. The valve 125 may comprise a pathway 130, wherein the pathway 130 allows fluid to pass from the second end of the regulator 105 to the first end of the regulator 105 while the valve 125 is closed. The apparatus may also comprise a flow detector 115, wherein the flow detector 115 is capable of sensing when the patient interface 110 is in contact with a liquid and causing the valve 125 to open, thereby allowing full flow of fluids from the second regulator end to the first regulator end.

Embodiments may also relate to a method for controlling medical suction, the method comprising obstructing the full flow of fluid from the second end of a vacuum regulator 105 to the first end of the vacuum regulator 105 using a valve 125, wherein the valve 125 comprises a small pathway 130 which allows a baseline fluid flow while the valve 125 is closed. The method may also comprise detecting when a patient interface 110, fluidly connected to the second end of the vacuum regulator 105, is in contact with a liquid and causing the valve 125 to open in response to detecting the patient interface 110 in contact with a liquid, thereby allowing full flow from the second end of the regulator 105 to the first end of the regulator 105.

The invention claimed is:

1. A medical suction regulator apparatus for use with a vacuum source and a patient interface, the apparatus comprising:
 a vacuum regulator comprising a valve arranged and designed to be fluidly connected between the vacuum source and the patient interface, a first end of the regulator is arranged and designed to be connected to the vacuum source and a second end of the regulator is arranged and designed to be connected to the patient interface;
 a pathway, wherein the pathway allows a baseline fluid flow from the second end of the regulator to the first end of the regulator while the valve is closed;
 a flow detector, wherein the flow detector is arranged and designed to sense when a liquid enters the patient interface and causes the valve to open, thereby allowing full flow of fluids from the second end of the regulator to the first end of the regulator.

2. The apparatus of claim 1, wherein the pathway is an orifice in the valve.

3. The apparatus of claim 2, wherein the orifice has a diameter between approximately 0.01 and 0.04 inches.

4. The apparatus of claim 1, wherein the sensing is done by way of detecting changes in flow through the pathway.

5. The apparatus of claim 1, further comprising a timer which closes the valve after a pre-determined time, thereby terminating the full flow of fluids from the second end of the regulator to the first end of the regulator and restoring flow to the baseline fluid flow.

6. The apparatus of claim 5, wherein the pre-determined time is between approximately 10 seconds and 30 seconds.

7. The apparatus of claim 1, wherein the flow detector comprises an electrical circuit.

8. The apparatus of claim 7, wherein a default position of the valve is open, providing fail-safe operation in case of a malfunction.

9. The apparatus of claim 1, wherein the valve is actuated electronically.

10. The apparatus of claim 1, wherein the valve is actuated mechanically.

11. The apparatus of claim 1, wherein the entire apparatus is packaged in a small portable housing.

12. The apparatus of claim 1, wherein the flow detector may be manually overridden to produce full flow in an emergency.

13. The apparatus of claim 1, wherein the apparatus is integrated into another medical device.

14. The apparatus of claim 1, wherein the pathway is a secondary pathway bypassing the valve and connecting the second end of the regulator to the first end of the regulator.

15. A method for controlling medical suction while using a vacuum source, the method comprising:
 connecting a first end of a vacuum regulator to the vacuum source;
 connecting a second end of the vacuum regulator to a patient interface;
 providing a valve between the first and second ends of the vacuum regulator,
 obstructing the full flow of a fluid from the second end of the vacuum regulator to the first end of the vacuum regulator using the valve, wherein the valve comprises a pathway which allows a baseline fluid flow while the valve is closed;
 detecting when a liquid enters the patient interface, fluidly connected to the second end of the vacuum regulator;
 causing the valve to open in response to detecting the liquid entering the patient interface, thereby allowing full flow from the second end of the vacuum regulator to the first end of the vacuum regulator.

16. The method of claim 15, further comprising closing the valve after a pre-determined period of time.

17. A method for controlling medical suction, the method comprising:
 providing a vacuum regulator having a first end, a second end and a valve, the first and second ends in fluid communication with one another;

providing the valve between the first and second ends such that the valve is in fluid communication with the first and second ends, the valve having a first position allowing full flow of a fluid and a second position allowing a baseline fluid flow;

connecting the first end of the vacuum regulator to a vacuum source and providing fluid communication between the first end of the vacuum regulator and the vacuum source;

connecting the second end of the vacuum regulator to a patient interface and providing fluid communication between the second end of the vacuum regulator and the patient interface;

maintaining the valve in the second position allowing a baseline fluid flow from the second end to the first end of the vacuum regulator when a liquid has not entered the patient interface;

detecting when the liquid enters the patient interface;

causing the valve to move to the first position in response to detecting the liquid entering the patient interface, thereby allowing full fluid flow from the second end of the regulator to the first end of the regulator.

18. The method of claim 17, wherein the step of detecting when the liquid enters the patient interface comprises detecting a change in pressure in the vacuum regulator.

* * * * *